United States Patent [19]

Gerstein

[11] 3,990,991

[45] Nov. 9, 1976

[54] SHAMPOO CONDITIONER FORMULATIONS

[75] Inventor: Terry Gerstein, Merrick, N.Y.

[73] Assignee: Revlon, Inc., New York, N.Y.

[22] Filed: Nov. 4, 1975

[21] Appl. No.: 628,599

Related U.S. Application Data

[63] Continuation-in-part of Ser. No. 438,879, Feb. 1, 1974, abandoned, which is a continuation-in-part of Ser. No. 372,590, June 22, 1973, abandoned.

[52] U.S. Cl. .............................. 252/542; 252/546; 252/547; 252/DIG. 13; 424/70
[51] Int. Cl.² ...................... C11D 1/58; A61K 7/06
[58] Field of Search ............. 424/70; 252/541, 542, 252/547, DIG. 1, DIG. 13

[56] References Cited
UNITED STATES PATENTS

| | | | |
|---|---|---|---|
| 3,156,656 | 11/1964 | Libby | 252/542 |
| 3,322,676 | 5/1967 | Hiestand | 252/542 |
| 3,452,042 | 6/1969 | Mannheimer | 424/70 |
| 3,472,840 | 10/1969 | Stone et al. | 260/231 |
| 3,578,719 | 5/1971 | Kalopissis et al. | 424/70 X |
| 3,808,329 | 4/1974 | Bolich et al. | 424/70 |

*Primary Examiner*—Thomas J. Herbert, Jr.
*Attorney, Agent, or Firm*—Leon E. Tenenbaum

[57] ABSTRACT

Aqueous shampoo-conditioner formulations having good cleansing, foaming, conditioning and detangling properties are provided. These formulations contain from about 4 to 25% by weight of an amphoteric surfactant, 4.5 to 25% by weight of a cryptoanionic surfactant, and from about 0.1 to 5% by weight of a cationic surfactant.

10 Claims, No Drawings

SHAMPOO CONDITIONER FORMULATIONS

This application is a continuation-in-part application of patent application Ser. No. 438,879, filed Feb. 1, 1974, now abandoned which is a continuation-in-part application of patent application Ser. No. 372,590, filed June 22, 1973, now abandoned.

This invention relates to formulations for application to hair. It particularly relates to formulations having both the desirable cleansing and foaming properties of a shampoo and the detangling and conditioning properties of a cream rinse.

Until recently the desirable properties of both a shampoo and a cream rinse could not be provided in a single formulation, and separate shampoo and cream rinse preparations had to be used if the desirable properaties of each of these preparations were to be obtained. Claims have recently been made that a shampoo formulated to contain Polymer JR Resin, a water-soluble cationic cellulosic resin described in U.S. Pat. No. 3,472,840, possessed the desirable properties of both a shampoo and a cream rinse.

However, although such preparations do clean and condition the hair, their detangling effects leave much to be desired. At best, these preparations, which contain in addition to Polymer JR Resin, triethanolamine lauryl sulfate and lauric diethanolamide, are inefficient detanglers when compared to cream rinses used independently. Furthermore, these preparations are formulated at an alkaline pH because not only do the anionic and alkanolamide surfactants function better on the alkaline pH side, but they are chemically unstable at acid pH. It is, however, preferable to use preparations of lower alkalinity for the hair.

It is, accordingly, an object of the present invention to provide a shampoo-conditioner formulation for hair, which not only cleans and conditions the hair but also serves as an efficient detangler.

It is another object of the present invention to provide a shampoo-conditioner formulation for hair, which has good foaming properties.

It is a further object of the present invention to provide a shampoo-conditioner formulation for hair, that is stable at pH from about 3.0 to 7.1, as well as at pH's up to about 8.5.

It has now been discovered that an aqueous composition comprising an amphoteric surfactant, a cryptoanionic surfactant, and a cationic surfactant has the desirable cleansing and foaming properties of a shampoo and the conditioning and detangling properties of a cream rinse.

As amphoteric surfactants I use the MIRANOL type surfactants. These are substituted imidazolines having as substituents, a long chain fatty acid radical and radicals containing hydrophlic groups. These surfactants are described in a technical and product development data report, "The MIRANOL Amphoteric Surface Active Agents", 5th Edition, 1967, published by the Miranol Chemical Company, Inc. The preferred amphoteric surfactant is MIRANOL C2MSF wherein the long chain fatty acid radical is a coconut fatty acid and the hydrophylic groups are carboxyls.

This surfactant has the structure

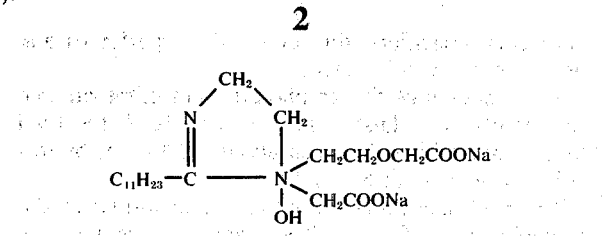

Other suitable amphoteric surfactants include amidobetaines such a Tegobetaine C, sarcosinates such as sodium lauryl sarcosinate, and long chain N-alkyl derivatives of beta-aminopropionic acid.

Crytoanionic surfactants as described in SANDOPAN DTC, a trade bulletin of Sandoz Chemical Works, New York, New York, are compounds of the formula $$R-O-(R_1O)_n-(CH_2)_m-CO_2H$$

wherein R is along chain alkyl group, $R_1$ is ethylene or propylene, $n$ has a value of from about 3 to 9, and $m$ is at least 1. In practicing the invention I prefer to use SANDOPAN DTC which is a substance of the formula $$R-O-(CH_2CH_2O)_n-CH_2-CO_2H$$

wherein R contains 13 carbon atoms and $n$ has a value of about 6.5.

Cationic surfactants are nitrogen compounds, such as quaternary ammonium compounds, betaines, amine oxides, salts of fatty amines, and the like, having surfactant properties. In the practice of this invention I prefer to use quaternary ammonium compounds. These compounds include long chain quaternary ammonium salts as, for example, stearyl-dimethyl-benzylammonium chloride, lauryl-dimethyl-benzylammonium bromide, cetyl-pyridinium chloride, and the like, and polymeric substances carrying quaternary ammonium groups. Examples of such polymeric sustances are the Polymer JR Resins and GAFQUATS.

The Polymer JR Resins are water-soluble cationic cellulose ethers having a chain of anhydroglucose units with substituent groups pendant therefrom spaced along the chain, each of said groups carrying a quaternary ammonium group. The structure and preparation of these surfactants are described in U.S. Pat. No. 3,742,840. The molecular weights of these surfactants vary over a wide range, and while all such surfactants have been found suitable in the practice of the present invention, the preferred surfactant is the JR-30M resin which has a molecular weight of about 30,000.

GAFQUATS is the trademark for quaternium-23 compounds which are copolymers of vinylpyrrolidone and diethylaminoethyl methacrylate quaternized with dimethyl sulfate. The molecular weights of these surfactants range from about 100,000 to about 1,000,000. As preferred GAFQUATS, I use GAFQUAT-734 which has a molecular weight of about 100,000 and is available as a 50% by weight solution in ethanol, and GAFQUAT-755 which has a molecular weight of about 1,000,000 and is available as a 20% by weight aqueous solution.

The aqueous compositions of the present invention are formulated to contain from about 4 to 25% by weight of the amphoteric surfactant, from about 4.5 to 25% by weight of the cryptoanionic surfactant, and from about 0.1 to 5% by weight of the cationic surfactant. If desired, additional agents such as sequestering agents, surfactants, U-V absorbents, conditioners, emolients, opacifiers, thickeners, dyes, perfumes and preservatives may be added.

The amounts of the amphoteric and cryptoanionic surfactants are adjusted so that the pH of the final formulation will be between about 3.0 to 8.5, preferably between about 6.2 and 6.9.

The invention will be more fully understood from the examples which follow. These examples are given by way of illustration and are not to be considered as limiting. In the examples the numbers refer to parts by weight. The number in parenthesis directly following an ingredient such as, for example, MIRANOL C2MSF (70), indicates that the material is present in an aqueous solution (ethanolic solution in the case of GAF-QUAT-734), the number in the parenthesis referring to the percent concentration.

| Example 1 | |
|---|---|
| Polymer JR-30M | 0.5 |
| Miranol C2MSF (70) | 15.0 |
| Sandopan DTC Acid (90) | 21.0 |
| Water | QS 100 |
| Example 2 | |
| Polymer JR-30M | 1.5 |
| Miranol C2MSF (70) | 11.0 |
| Sandopan DTC Acid (90) | 15.0 |
| Stearate Opacifier (Ethylene glycol distearate) | 2.0 |
| Methyl Parasept | 0.2 |
| Propyl Parasept | 0.05 |
| Protein Hydrolysate | 0.5 |
| Perfume Oil | 0.3 |
| FDC Yellow No. 5 (2) | 0.2 |
| Water | QS 100 |
| Example 3 | |
| Polymer Jr-400 | 2.0 |
| Miranol C2MSF (70) | 8.0 |
| Sandopan DTC Acid (90) | 11.0 |
| Ricinoleic Diethanolamide | 1.0 |
| Formalin Solution | 0.15 |
| Perfume Oil | 0.3 |
| Water | QS 100 |
| Example 4 | |
| Gafquat 755 (20) | 5.0 |
| Miranol C2MSF (70) | 11.0 |
| Sandopan DTC Acid (90) | 15.0 |
| Protein Hydorlysate | 0.5 |
| Disodium EDTA | 0.5 |
| Stearyl Dimethyl Amine Oxide (25% Active) | |
| Methyl Parasept | 0.2 |
| Propyl Parasept | 0.05 |
| Perfume Oil | 0.3 |
| Water | QS 100 |
| Example 5 | |
| Stearyl Dimethyl Benzyl Ammonium Chloride | 1.0 |
| Miranol C2MSF (70) | 11.0 |
| Sandopan DTC Acid (90) | 15.0 |
| Hydroxypropyl Cellulose | 1.0 |
| Formalin Solution | 0.15 |
| Perfume Oil | 0.3 |
| Water | QS 100 |
| Example 6 | |
| Polymer JR-400 | 1.0 |
| Coco Amido Alkyl Betaine (30) | 20.0 |
| Sandopan DTC Acid (90) | 5.0 |
| 70:30 Lauric-Myristic Diethanolamide | 5.0 |
| Ethoxylated Lanolin Alcohols —25 EtO | 1.0 |
| Formalin Solution | 0.15 |
| Perfume Oil | 0.3 |
| Water | QS 100 |
| Example 7 | |
| Polymer JR-125 | 1.0 |
| N-Coco-beta-amino propionic acid | 5.0 |
| Sandopan DTC Acid (90) | 5.0 |
| Stearyl Dimethyl Amine Oxide | 2.0 |
| Coconut Monoethanolamide | 5.0 |
| Propylene Glycol | 3.0 |
| Dowacil 200 | 0.1 |
| Perfume Oil | 0.3 |
| Water | QS 100 |
| Example 8 | |
| N-(Stearoyl-colamino-formyl- | 0.5 |
| methyl)-Pyridinium Chloride | |
| Miranol C2MSF (70) | 11.0 |
| Sandopan DTC Acid (90) | 15.0 |
| Polyvinylpyrrolidone-K90 | 5.0 |
| Dowacil 200 | 0.1 |
| Perfume Oil | 0.3 |
| Uvinul MS-40 (UV Absorbing Agent) | 0.05 |
| FDC Green No. 5 (2) | 0.03 |
| Water | QS 100 |
| Example 9 | |
| Stearylamidopropyl diethanolamine lactate | 2.0 |
| Miranol C2M-SF (70) | 15.0 |
| Sandopan DTC Acid (90) | 21.0 |
| Hydroxypropyl Cellulose | 1.0 |
| Formalin Solution | 0.1 |
| FD & C Green No. 5 (2) | 0.2 |
| Water | QS 100 |
| Example 10 | |
| Gluconamidopropyl dimethyl 2-hydroxyethyl ammonium chloride (60) | 5.0 |
| Sandopan DTC Acid (90) | 10.0 |
| Coco Amido Alkyl Betaine (30) | 15.0 |
| Miranol C2M-SF (70) | 7.3 |
| Lauric Diethanolamide | 2.0 |
| Disodium salt of Ethylenediaminetetraacetic Acid | 0.3 |
| Methyl Parasept | 0.2 |
| Propyl Parasept | 0.05 |
| Perfume Oil | 0.2 |
| Water | QS 100 |
| Example 11 | |
| GAFQUAT 734 (50) | 5.0 |
| Coco Amido Propyl Dimethyl Amine Oxide (30) | 8.0 |
| Sandopan DTC Acid (90) | 15.0 |
| Miranol C2M-SF (70) | 11.0 |
| Hydroxypropyl Cellulose | 2.0 |
| Glyco Amido Stearate | 3.0 |
| Dowacil 200 | 0.1 |
| FDC Red No. 19 (1) | 0.2 |
| Water | QS 100 |
| Example 12 | |
| GAFQUAT 755 (20) | 10.0 |
| Sandopan DTC Acid (90) | 15.0 |
| Isostearylamidopropyl diethanolamine | 4.0 |
| Coconut Diethanolamide | 5.0 |
| Tween 20 | 5.0 |
| Protein Hydrolysate | 1.0 |
| Dimethylol dimethyl hydantoin | 0.8 |
| Water | QS 100 |

These formulations of these examples had pH's falling within the range of 3.0 to 8.5.

The formulations were tested on hair and were found to have excellent cleaning, foaming, conditioning and detangling properties.

I claim:

1. An aqueous shampoo-conditioner formulation for hair, said formulation having a pH from about 3.0 to 8.5 and containing as essential ingredients from about 4 – 25% by weight of an amphoteric surfactant of the formula

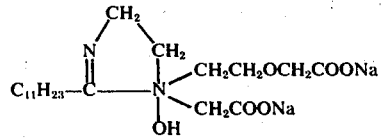

from about 4.5 to 25% by weight of a cryptoanionic surfactant of the formula $$R-O-(CH_2CH_2O)_n-CH_2CO_2H$$

wherein R is an alkyl group having 13 carbon atoms and n has a value of about 6.5, and from 0.1 to 5% of a cationic surfactant selected from the group consisting of water-soluble cellulosic ethers having a chain of anhydroglucose units with substituent groups each carrying a quaternary ammonium group pendant from and spaced along the chain, long chain quaternary ammonium compounds, and copolymers of vinylpyrrolidone and dimethylaminoethyl methacrylate quaternized with dimethyl sulfate.

2. A composition according to claim 1 wherein the pH is from about 6.2 to 6.9.

3. A composition according to claim 1 wherein the cationic surfactant is a water-soluble cellulose ether having a chain of anhydroglucose units with substituent groups carrying a quaternary ammonium group pendant from and spaced along the chain.

4. A composition according to claim 3 wherein the molecular weight of the water-soluble cellulose ether is about 30,000.

5. A composition according to claim 4 which contans 1.5% of the cationic surfactant, 7.7% of the amphoteric surfactant, and 13.5% of the cryptoanionic surfactant.

6. A composition according to claim 1 wherein the cationic surfactant is a long chain quaternary ammonium compound.

7. A composition according to claim 6 wherein the long chain quaternary ammonium compound is stearyl-dimethyl-benzylammonium chloride.

8. A composition according to claim 7 wherein the long chain quaternary ammonium compound is stearolcolamino-formyl-methylpyridinium chloride.

9. A composition according to claim 1 wherein the cationic surfactant is a copolymer of vinylpyrrolidone and diethylaminoethyl methacrylate quaternized with dimethyl sulfate.

10. A composition according to claim 9 wherein the molecular weight of the cationic surfactant is about 100,000 to 1,000,000.

* * * * *